(12) United States Patent
Shvartsburg et al.

(10) Patent No.: US 7,170,053 B2
(45) Date of Patent: Jan. 30, 2007

(54) METHOD AND APPARATUS FOR ION MOBILITY SPECTROMETRY WITH ALIGNMENT OF DIPOLE DIRECTION (IMS-ADD)

(75) Inventors: Alexandre A. Shvartsburg, Richland, WA (US); Keqi Tang, Richland, WA (US); Richard D. Smith, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 162 days.

(21) Appl. No.: 11/097,855

(22) Filed: Mar. 31, 2005

(65) Prior Publication Data

US 2006/0219889 A1 Oct. 5, 2006

(51) Int. Cl.
*H01J 49/40* (2006.01)
(52) U.S. Cl. ........................................ 250/287; 250/282
(58) Field of Classification Search ................ None
See application file for complete search history.

(56) References Cited

U.S. PATENT DOCUMENTS

| | | | |
|---|---|---|---|
| 5,905,258 A * | 5/1999 | Clemmer et al. ............ 250/287 |
| 6,107,624 A * | 8/2000 | Doring et al. .............. 250/286 |
| 6,495,823 B1 | 12/2002 | Miller et al. |
| 6,512,224 B1 | 1/2003 | Miller et al. |
| 6,727,495 B2 * | 4/2004 | Li .............................. 250/286 |
| 6,787,765 B2 | 9/2004 | Guevremont et al. |
| 6,831,273 B2 * | 12/2004 | Jenkins et al. ............. 250/287 |
| 2003/0213899 A9 | 11/2003 | Guevremont et al. |
| 2005/0040330 A1 | 2/2005 | Kaufman et al. |

FOREIGN PATENT DOCUMENTS

GB 2 393 849 A 4/2004

OTHER PUBLICATIONS

I.A. Buryakov, et al. Pis'ma ZH. Tekh. Fiz. vol. 17, pp. 60-65 (1991).
G.A. Eiceman, et al. International Journal of Mass Spectrometry 3 (2000) vol. 1, pp. 15-27.
Randy W. Purves, et al. et al. International Journal of Mass Spectrometry 197 (2000) 163-177.

(Continued)

*Primary Examiner*—Jack I. Berman
(74) *Attorney, Agent, or Firm*—James D. Matheson

(57) ABSTRACT

Techniques and instrumentation are described for analyses of substances, including complex samples/mixtures that require separation prior to characterization of individual components. A method is disclosed for separation of ion mixtures and identification of ions, including protein and other macromolecular ions and their different structural isomers. Analyte ions are not free to rotate during the separation, but are substantially oriented with respect to the drift direction. Alignment is achieved by applying, at a particular angle to the drift field, a much stronger alternating electric field that "locks" the ion dipoles with moments exceeding a certain value. That value depends on the buffer gas composition, pressure, and temperature, but may be as low as ~3 Debye under certain conditions. The presently disclosed method measures the direction-specific cross-sections that provide the structural information complementing that obtained from known methods, and, when coupled to those methods, increases the total peak capacity and specificity of gas-phase separations. Simultaneous 2-D separations by direction-specific cross sections along and orthogonally to the ion dipole direction are also possible.

62 Claims, 10 Drawing Sheets

Waveform Phase

OTHER PUBLICATIONS

C.A. Hill, et al., The Royal Society of Chemistry, The Analyst (2003) vol. 128, pp. 55-60.

Norris E. Bradbury, et al., Physical Review, vol. 49, pp. 388-393, Mar. 1, 1936.

Laura M. Matz, Elsevier, Talanta 54 (2001) 171-179.

G.R. Asbury, et al., International Journal of Mass Spectrometry vol. 2 (1999) 1-8, p. 2.

M.R. Gunner, et al., Biophysical Journal, vol. 78, Mar. 2000, pp. 1126-1144.

Clair J. Bramwell, et al., The Royal Society of Chemistry, The ANALYST, 2002, 127, pp. 1467-1470.

Shvartsburg, et al., American Society for Mass Spectrometry, 2004, 15, pp. 1487-1498.

Andreas Mandelis, et al., Analytical Sciences, Apr. 2001, vol. 17, Special Issue.

PCT International Search Report and Written Opinion (Mar. 8, 2006).

PH. Dugourd, et al, Review of Scientific Instruments, vol. 68, No. 2, Feb. 1997, pp. 1122-1129, XP002391236, p. 1123, col. 1-p. 1125, col. 1; fig. 1.

R.A. Dressler, et al., Journal of Chemical Physics, vol. 87 #10, Nov. 15, 1987, XP009069766 abstract.

Shvartsburg, et al., Analytical Chemistry, Dec. 2004, vol. 76 #24 XP002391237 (the whole document).

P. Poulain, et al, Chemical Physics Letters, vol. 401, pp. 1-6, XP002391236, Nov. 23, 2004.

* cited by examiner

METHOD AND APPARATUS FOR ION MOBILITY SPECTROMETRY WITH ALIGNMENT OF DIPOLE DIRECTION (IMS-ADD)

This invention was made with Government support under Contract DE-AC05-76RL01830 awarded by the U.S. Department of Energy. The Government has certain rights in the invention.

FIELD OF THE INVENTION

The present invention relates generally to techniques and instrumentation for analytical characterization of substances, including complex samples/mixtures that require separation prior to analysis of some or all components. More particularly, the invention relates to separation of ionic mixtures and identification of ions in the gas phase, including protein and other macromolecular ions and their different structural or conformational isomers, using ion mobility spectrometry.

BACKGROUND OF THE INVENTION

The central challenge of analytical chemistry is rapid and accurate identification and quantitation of all components of complex mixtures, starting from minute sample amounts. This has typically been achieved using mass spectrometric (MS) tools that offer an exceptional sensitivity, specificity, and dynamic range. However, even with the formidable power of modern MS, most real-world samples require prior separations. Those separations had usually been performed in the condensed phase (liquid and solid), e.g. liquid chromatography (LC), capillary electrophoresis (CE), capillary isoelectric focusing (CIEF), and gel electrophoresis in one or two dimensions such as SDS polyacrylamide gel electrophoresis (SDS-PAGE) and 2-D gel. Since the 1980-s, two gas-phase separations techniques based on ion mobility have been developed and coupled to MS—Ion Mobility Spectrometry (IMS), e.g. by Bowers et al. (*Science* 260, 1446, 1993), and Field Asymmetric waveform Ion Mobility Spectrometry (FAIMS) detailed, e.g., by Buryakov et al. (*Sov. Tech. Phys. Lett.* 17, 446, 1991). A major attraction of IMS and FAIMS is a huge throughput gain over condensed-phase separations allowed by the high speed of ion motion in gases compared to that in liquid or solid media. The other advantage is that both IMS and FAIMS generally distinguish structural/conformational isomers, which only rarely happens in LC and other condensed-phase separations. Finally, IMS is not merely a separation tool, but a broadly applicable structural probe that has provided unique insights into the structure and polymorphism of gas-phase ions and the dynamics of their isomerization and conformational transitions (e.g., Shvartsburg et al., *Chem. Soc. Rev.* 30, 26, 2001).

Further, recent discoveries in proteomics and structural biology point to the multiplicity of conformations for otherwise identical proteins that critically affect protein function. The term conformation refers to any of the spatial and/or structural configurations of an ion or molecule obtained by rotation about one or more bonds or of an assembly of ions or molecules (i.e. macromolecular complex) obtained by mutual displacement of constituents, which includes different tertiary and quaternary protein structures. The ability to distinguish, separate, and characterize all such conformations is necessary for complete proteomic analyses. Those cannot be achieved within either of the two known proteomics paradigms—(1) bottom-up and (2) top-down, as the information about 3-D protein structure is lost in the first step of analysis—proteolytic digestion in (1) and fragmentation in (2) that is generally non-specific to the original conformation (e.g., Badman et al., *J. Am. Soc. Mass Spectrom.* 13, 719, 2002).

Elucidation of protein conformations by known methods of structural biology, including, e.g., x-ray crystallography and NMR, while accurate and reliable, depends on crystallizing a protein. Certain important proteins (e.g., prions implicated in transmissible spongiform encephalopathies and amyloido-genic peptides) cannot be crystallized currently. More generally, those techniques require purifying each protein of interest in macroscopic quantities that is often impossible or impractical, and take substantial time to solve each protein structure. Hence there is a need for methods to characterize the structure of any protein without crystallization, simultaneously for all proteins in a complex biological matrix without prior purification, and with sensitivity and speed/throughput comparable to those of modern proteomic analyses. Such methods should preferably be compatible online with known proteomics protocols that allow accurate protein identification and quantitation, including the elucidation of post-translational modifications. There also is a strong need for methods probing protein conformation as a function of time, protein charge state, number of structural waters or other binding ligands, and solution conditions such as temperature, solvent composition, acidity, ionic strength, and abundance of specific chemicals (for example, heme ions or other proteins/chaperones). This capability is not provided by known structural biology tools.

IMS separates and identifies gas-phase ions on the basis of ion mobility (K) that determines ion drift velocity (v) under the influence of a moderate electric field (E) via equation [1]:

$$v = KE \qquad [1]$$

The raw mobility is often converted to standard temperature and pressure (STP) conditions by defining the reduced mobility ($K_o$) via equation [2]:

$$K_o = K(P/760) \times (273/T) \qquad [2]$$

where P is the buffer gas pressure. The mobility is related to orientationally averaged collision cross-section $\Omega_{Avg}^{(1,1)}$ (rigorously the 1$^{st}$-order collision integral) of the ion and gas molecule via the Mason-Schamp equation [3]:

$$K_o = (3q/16N) \times (2\pi/\mu kT)^{1/2} / \Omega_{Avg}^{(1,1)} \qquad [3]$$

where q is the ion charge, N is the gas number density, μ is the reduced mass of the analyte ion/gas molecule pair, k is the Boltzmann constant, and T is the gas temperature. The quantity $\Omega_{Avg}^{(1,1)}$ for any ion-gas pair can be computed using various treatments known in the art, including but not limited to projection approximation, exact-hard-spheres-scattering (EHSS), trajectory calculations, and scattering on electron density isosurfaces (SEDI), (e.g., Shvartsburg et al., *J. Phys. Chem. A* 104, 6152, 2000), enabling characterization of ions by matching mobilities calculated for trial geometries with measurements (e.g., Jackson et al., *Phys. Rev. Lett.* 93, 013401, 2004). Critically to this disclosure, ion mobilities in IMS depend on the orientationally averaged cross sections, because the electric field is far too weak to measurably interfere with free thermal rotation of realistic analyte ions in any direction.

IMS analyses are typically performed using drift tubes with a weak constant DC field (drift field) inside created by an electrode stack, across which the drift voltage is partitioned by a resistor chain (e.g., Rokushika et al., Anal. Chem. 57, 1902, 1985). Some applications use a non-uniform DC field (e.g., Valentine et al., Anal. Chem. 75, 6202, 2003). In some designs, the DC field may be set by computer-controlled voltages (Blanchard, U.S. Pat. No. 4,855,595), thereby allowing separations that employ time-dependent fields such as a traveling wave (Martin et al., U.S. Pat. No. 5,789,745). When IMS is used as a structural tool, the magnitude of E is limited by the need to remain in the low-field limit where K(E) is constant and equation [3] applies (e.g., Shvartsburg et al., J. Chem. Phys. 108, 2416, 1998). Also, the resolution deteriorates at high E, because of longitudinal ion diffusion accelerating at high E/N (Verbeck et al., J. Am. Soc. Mass Spectrom. 15, 1320, 2004). The resolution may be somewhat improved by a buffer gas counterflow inside IMS that lengthens the separation time (e.g., Sysoev et al., Rapid Commun. Mass Spectrom. 18, 3131, 2004). Alternatively to the time-domain mode, there is a frequency-domain mode wherein the IMS spectrum is a Fourier transform of raw data obtained by scanning the frequency of ion injections into IMS (e.g., Knorr et al., Anal. Chem. 57, 402, 1985).

IMS is commonly used in conjunction with MS, and the IMS/ToF combination that allows simultaneous separations in IMS and MS dimensions is particularly attractive. In IMS/ToF systems, the dynamic range and/or IMS resolution may be improved using position-sensitive and multi-anode ToF detectors (Fuhrer et al., US 2003/0001087 A1). Also, MS analyzers coupled to IMS may be further enhanced by ion spectroscopies, such as photoelectron spectroscopy (PES) and photodissociation spectroscopy (Fromherz et al., Phys. Rev. Lett. 89, 083001, 2002). Another approach to increasing specificity is dissociating ions at the end of or immediately following IMS separation, with the MS analyses performed on fragments. Dissociation may be induced by means including, but not limited to, collision cells, orifice-skimmer cones, or high-field (split-field) regions (Lee et al., Anal. Chem. 73, 3549, 2001).

As a pulsed technique, IMS requires introducing analyte ions in discrete packets, thus continuous ion beams must be converted into pulses prior to injection into IMS. This conversion can be accomplished using many means known in the art, including, but not limited to, a mechanical shutter, a pulsed ion retarding/repelling wires, mesh or electrode(s), a Bradbury-Nielsen gate (e.g., C. Wu et al., Anal. Chem. 72, 391, 2000), a split lens for transverse ion deflection (Dugourd et al., Rev. Sci. Instrum. 68, 1122, 1997) or other electrostatic shutter, and a spherical FAIMS trap or t-FAIMS (Guevremont et al., J. Am. Soc. Mass Spectrom. 12, 1320, 2001). At moderately high pressure, ions may be accumulated and periodically injected into IMS using an ion funnel (Smith et al., U.S. Pat. No. 6,107,628) and specifically an hourglass funnel optimized for pulsed ion transmission (Smith et al., U.S. Pat. No. 6,818,890).

Mobilities measured in IMS can be matched with values calculated for candidate geometries. Those values may be computed using the expression for scattering angle of buffer gas atoms on the ion ($\chi$) as a function of ion-atom relative velocity g, impact parameter b, and the angles $\theta$ and $\gamma$ defining the collision geometry (e.g., Shvartsburg et al., J. Chem. Phys. 108, 2416, 1998). The collision cross section $\Omega^{Avg(1,1)}$ is produced by integration of function $\chi(g, b, \theta, \gamma)$ over all four variables (with $\theta$ and $\gamma$ uniformly distributed), for example via the Monte Carlo integration scheme (Mesleh et al., J. Phys. Chem. 100, 16082, 1996).

While IMS is capable of separating gas-phase ions and providing structural information, analytes commonly contain multiple conformations that are not distinguished because of limited peak capacity. Also, measured cross sections often lack the specificity necessary to fully characterize ion geometries, because of limited instrumental resolution and accuracy, and finite precision of mobility calculations for candidate geometries. The orientational averaging in IMS reduces the difference in cross section of different geometries and thus collapses the available separation space, and augments the correlation of cross-section to molecular volume and thus to the mass. As a result, ion mobility and mass become significantly correlated, particularly for ions of specific charge state and chemically similar/homologous species. This correlation is undesirable, as it reduces the orthogonality between IMS separations and MS and hence the total peak capacity of IMS/MS analyses. This problem of IMS/MS is well recognized in the art (Ruotolo et al., J. Mass Spectrom. 39, 361, 2004).

FAIMS is the other known technique for separating and identifying gas-phase ions. As reported, e.g., by Purves et al. (Rev. Sci. Instrum. 69, 4094, 1998), FAIMS exploits the fact that ion mobility is a function of electric field. That function may be expressed via equation [4]:

$$K_0(E)=K_0(0)\times(1+a(E/N)^2+b(E/N)^4+c(E/N)^6+\ldots) \quad [4]$$

Sixth and higher order terms are generally insignificant at practical field intensities. As E increases, K(E) may increase, decrease, or first increase and then decrease at still higher E values. A periodic asymmetric waveform at time-dependent potential $U_D(t)$ is applied to one or more electrode pairs. The integral of $U_D(t)$ over each period is null, but time-averaged positive and negative voltages differ. The peak amplitude of $U_D(t)$ must suffice to induce a requisite difference in ion mobility between high and low half-cycles. This waveform pushes all ions introduced into the analytical gap between the electrodes towards either electrode where the ions are destroyed by neutralization. Such asymmetric waveforms may be generated by two-frequency resonance circuits (Krylov, Instrum. Exp. Tech. 34, 859, 1991). FAIMS electrodes may have various shapes, including planar, cylindrical, and spherical. In the cylindrical geometry, ions may focus to the analytical gap median (Buryakov et al., Russian patent SU 1,485,808). Particular ion species are prevented from drifting towards either electrode and centered in the analytical gap by a compensation voltage (CV) that cancels the net ion drift due to $U_D(t)$. The CV value is a unique property of an ion species. FAIMS is capable of separating ion mixtures and identifying ions based on CV, but also suffers from limited resolution and specificity. No structural information about ions can currently be extracted from FAIMS data since no reliable methods for high-field mobility calculations on polyatomic ions presently exist.

The resolution and peak capacity of FAIMS separations may be enhanced in certain gas mixtures in which high-field ion mobilities exhibit a significant non-Blanc behavior (Shvartsburg et al., Anal. Chem. 76, 7366, 2004) or buffer gases containing water or volatile organic vapors (e.g., Buryakov et al., Russian Patent SU 1,627,984).

In conventional FAIMS, ions are carried through the device by a gas flow. In a longitudinal field driven FAIMS, as described by Miller et al. (U.S. Pat. Nos. 6,512,224, 6,815,669), that flow is replaced by a longitudinal electric field created by segmented FAIMS electrodes or separate electrodes provided in addition to FAIMS electrodes.

Accordingly, there remains a need for methods and devices that provide separation and identification of gas-phase ions, including macromolecular ions and structural and conformational isomers thereof, with high resolution and accuracy, and significant orthogonality to known IMS and FAIMS separations, as well as to MS. In particular, new methods should preferably yield data that can be related to molecular geometries with a high degree of specificity.

SUMMARY OF THE INVENTION

Accordingly, it is an object of the invention to provide a new method and apparatus for separation of ion mixtures and identification of ions in the gas phase. It is another object of the invention to provide a method that is substantially orthogonal to known IMS and FAIMS gas-phase separations. Another object of the invention is to provide a method for obtaining structural information about ions that is complementary to that derived from known methods (such as IMS) and can be related to specific ion geometries. Still yet another object of the invention is for the method to exhibit low ion losses and thus have a high sensitivity, making it a practical tool of broad utility. A further object of the invention is to provide a ready coupling of the method and apparatus to mass-spectrometry (MS) analyses by any MS analyzer, making the new method compatible with known proteomics approaches. Finally, a further object of the invention is to provide for efficient coupling of the method and apparatus to IMS and/or FAIMS in various arrangements, enabling two- and even three-dimensional gas-phase separations and identification of ions for added peak capacity and specificity.

The above enumerated and other objects of the invention are achieved by the disclosed novel method and apparatus for analytical characterization of substances, including complex samples/mixtures that require separation prior to analysis of individual components. The invention generally employs the separation and identification of ions based on their mobility in gases. The fundamental novel feature of the presently disclosed method and apparatus is that the orientation of analyte ions relative to the drift direction is substantially non-random, creating Ion Mobility Spectrometry with Alignment of the Dipole Direction (IMS-ADD). The desired orientational preference is achieved by aligning the total molecular dipole by a strong electric field applied along the desired alignment axis.

In an embodiment, the invention comprises a pair of segmented electrodes with the analytical gap between them, at least a portion of which is filled with a buffer gas. The electrodes carry voltages establishing an electric field inside the gap. The field comprises a first (relatively weak) component (the drift field) superposed over a second (relatively strong) component (the aligning field) directed along an axis (the alignment axis) disposed at a defined angle relative to the drift field. An ion source introduces into the gap a discrete packet of analyte ions, including at least one ion species of interest. The second component substantially aligns the dipoles of at least some analyte ions along its direction, and the first component (weak enough to not materially affect the dipole alignment) pulls thus aligned ions in its direction, thus measuring the collision cross sections of ions with gas molecules along a specific orientation defined by said alignment angle, rather than orientationally-averaged cross sections. Analyte ions are spatially separated and/or identified based on the direction specific cross sections.

In another embodiment, to avoid a rapid removal of ions from the IMS-ADD analytical gap, the electric field aligning the dipole is oscillatory.

In an example, the oscillatory waveform is symmetric with respect to zero field.

In another example, the oscillatory waveform is asymmetric with respect to zero field.

In an embodiment of the method, the invention comprises providing a plurality of electrodes containing a space therebetween, the electrodes carrying voltages establishing an electric field over at least a part of the space, the field comprising a first component along a first (drift) axis superposed over a second substantially stronger component along a second (alignment) axis, the second axis disposed at a defined angle relative to the first axis; filling at least a portion of the space with a buffer gas; periodically introducing into the space a discrete packet of analyte ions comprising at least one species therein having an electric dipole, wherein the second field component substantially aligns the dipole(s) of the at least one species along the second axis, and the first component pulls the substantially aligned ions along the direction of the first axis; and whereby the ions are spatially separated or identified based on a measured collision cross section with gas molecules that is other than averaged equally over all spatial orientations and is direction-specific depending on the defined angle.

DETAILED DESCRIPTION

Figure 1A:
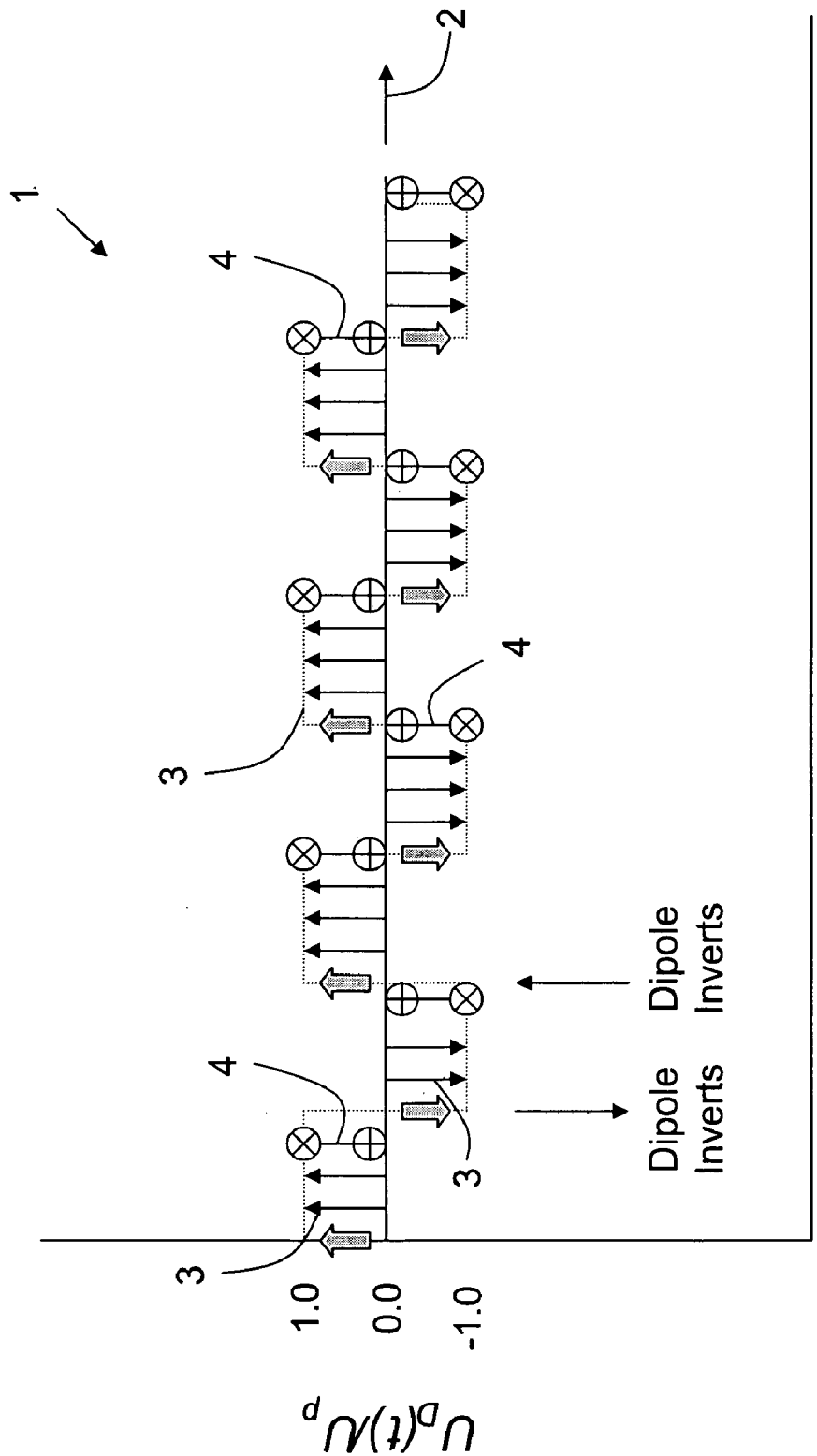
FIGS. 1a–1b illustrate a symmetric waveform applied to the electrode pair in IMS-ADD (in addition to the longitudinal voltage component), according to two embodiments of the invention: an ideal rectangular profile (a), a bisinusoidal profile created by superposition of two harmonics (b).

While the present disclosure is exemplified by specific embodiments, it should be understood that the invention is not limited thereto, and variations in form and detail may be made without departing from the spirit and scope of the invention. All such modifications as would be envisioned by those of skill in the art are hereby incorporated.

The present invention employs the separation and identification of ions based on their mobility in gases, wherein the spatial orientation of analyte ions relative to the drift vector is specific, yielding Ion Mobility Spectrometry with Alignment of the Dipole Direction (IMS-ADD). In IMS-ADD, analyte ions are not free to rotate during separation, but are substantially oriented ("aligned") with respect to the drift direction. Desired orientations of the total molecular dipole along a particular alignment axis (disposed at a particular angle β relative to the drift field, for example but not necessarily β=90°) are achieved using a strong electric field applied along that axis. The term "aligned" with respect to a dipole means that its spatial orientation is significantly non-random, but need not imply it to be completely fixed. In particular, dipoles in the "hindered rotation" or "pendular" states known in the classical mechanics are "aligned" for the purpose of this disclosure. The term "total molecular dipole" or simply "dipole" herein means any superposition of the permanent electric dipole, a "pseudo-dipole"—the manifestation of a torque on an ion with non-coincident center-of-mass and center-of-charge experiencing an electric field in media, and/or an induced dipole determined by ion polarizability. The strong electric field "locks" ion dipoles with moments exceeding a threshold value, depending on the field intensity and buffer gas temperature as discussed below.

Thus aligned ions travel through IMS-ADD under the influence of another electric field component that is sufficiently weak to not materially affect the dipole alignment. Different ions drift with different velocities, and thus spatially separate and reach the device terminus at different times. For each distinguished ion type, the drift velocity is measured by known means (for example, as in conventional IMS by timing the passage of discrete ion packets through a known distance) and related to ion mobility via equations [1, 2] known in the art. However, the mobility in IMS-ADD is determined not by orientationally-averaged cross section $\Omega_{Avg}^{(1,1)}$ as in IMS, but by a direction-specific quantity $\Omega_{Dir}^{(1,1)}$ that depends on β [5]:

$$K_o = (3q/16N) \times (2\pi/\mu kT)^{1/2} / \Omega_{Dir}^{(1,1)}(\beta) \qquad [5]$$

The case of those axes being perpendicular at β=90° (wherein $\Omega_{Dir}^{(1,1)}$ is denoted $\Omega^\perp$) permits the most straightforward embodiment of the invention, described hereafter. However, the invention is not limited thereto, and any β (including β=0 when those axes are coincident, resulting in $\Omega_{Dir}^{(1,1)}$ denoted $\Omega\|$) are embodied within the scope of this disclosure.

Though this is not a prerequisite for practicing the invention, in an exemplary embodiment the aligning electric field in IMS-ADD is oscillatory to avoid a rapid removal of ions from the analytical gap. With an alternating electric field, the mean (i.e., time-averaged) extent of dipole alignment is maximized by minimizing the fractional duration of low field intensity during the cycle. This is achieved by a rectangular waveform with the shortest rise and fall times possible. However, other waveforms such as harmonic or superposition thereof may be used for reasons of limited power, engineering simplicity, or cost. Thus, the invention is by no means restricted to any specific time-dependent profile of strong electric field component, as long as it effects a sufficient alignment of analyte ion dipoles under experimental conditions.

In an embodiment of the invention, the waveform (rectangular, sinusoid-based, or any other) is symmetric with respect to zero field [FIG. 1]. In particular, the frequency, amplitude, and/or profile of that waveform may be adjustable. This capability may be used to (i) vary the extent of dipole alignment over any range from zero to ~100%, and specifically to effect a transition from conventional IMS to IMS-ADD, and/or (ii) measure the direction-specific cross section along the axis of dipole alignment by filtering out ions with that cross section below a certain threshold that may be set or scanned. Mode (ii) would enable 2-D IMS-ADD separations by direction-specific cross sections along the aligning and drift fields simultaneously.

Figure 1B:
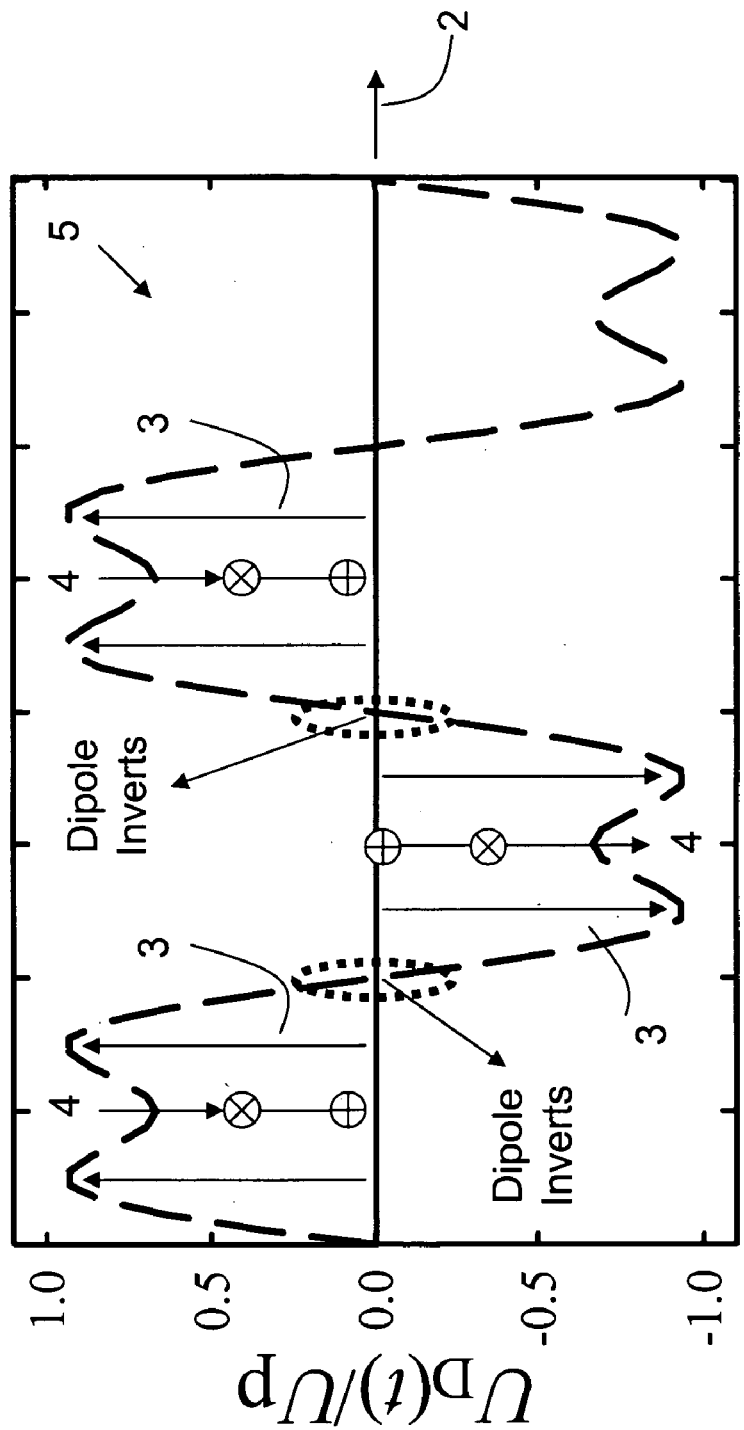

FIG. 1a illustrates an ideal rectangular symmetric waveform 1, applied to an IMS-ADD device as described hereafter in addition to the longitudinal drift field component 2, according to an embodiment of the invention. The strong aligning field component 3 orients the dipoles of analyte ions 4 thereby defining the alignment axis 3 at an angle to the drift axis 2. FIG. 1b illustrates a realistic symmetric waveform 5 comprising a superposition of harmonic oscillations, applied to an IMS-ADD device as described hereafter in addition to the longitudinal drift field component 2, according to another embodiment of the invention. The waveform in FIG. 1b is an addition of two harmonic oscillations with 2:1 frequency ratio, but harmonics with other ratios and/or other number of harmonics may equally be used without limitation.

In another embodiment, the waveform has an asymmetric profile [FIG. 2] (with a variable DC compensation voltage—CV added) as employed in FAIMS separations. When the electric field is strong enough to both align the dipole and induce FAIMS filtering through the K(E) dependence, scanning CV permits concurrent FAIMS and IMS-ADD separations in the instant embodiment: ions separate along the alignment axis in the FAIMS dimension and the drift axis in IMS-ADD dimension simultaneously. The asymmetric profile may be of any type including, but not limited to, rectangular, bisinusoidal, or clipped-sinusoidal. The rectangular waveform that maximizes the mean dipole alignment is also most efficient for FAIMS separations, particularly when the "high-to-low ratio" is about two (Shvartsburg et al., J. Am. Soc. Mass Spectrom. 16, 2, 2005).

Figure 2A:
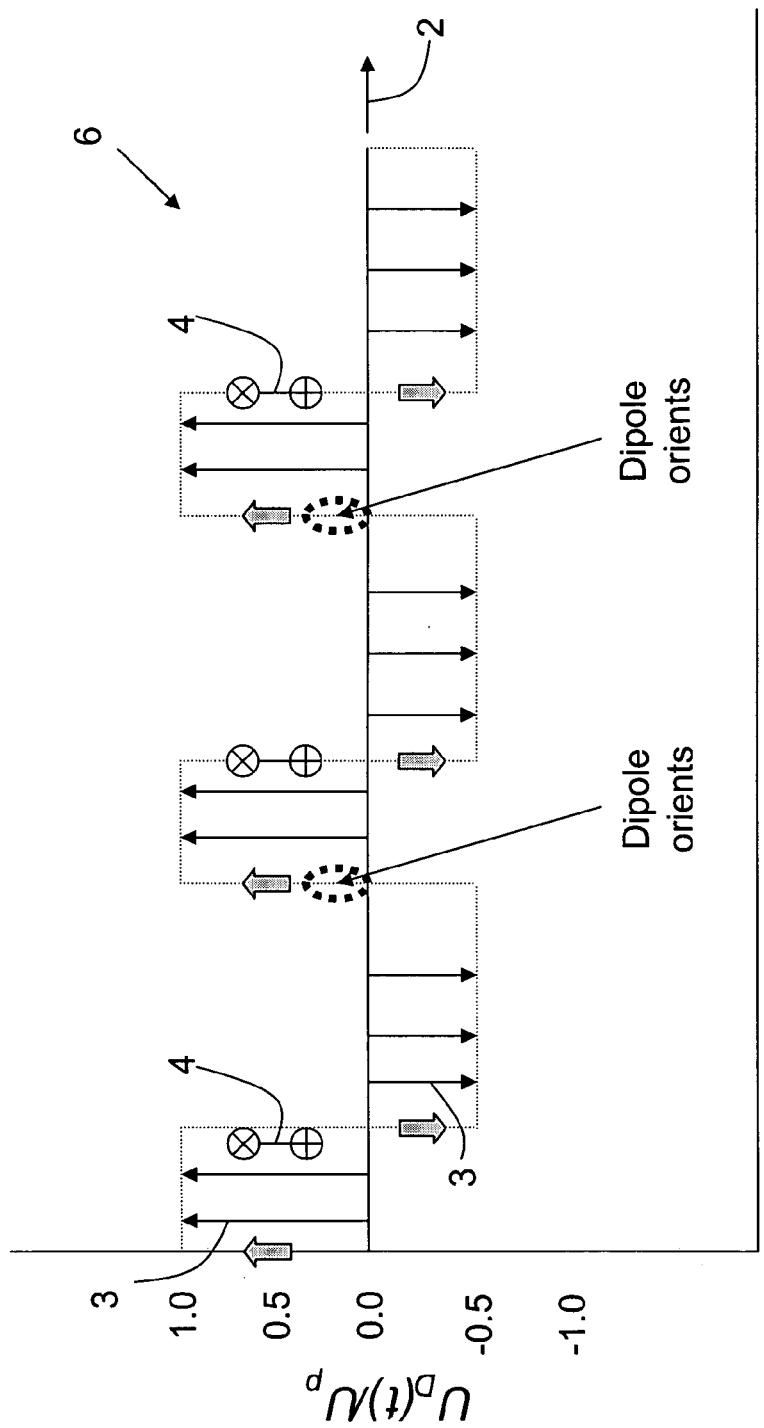
FIGS. 2a–2b illustrate an asymmetric waveform applied to the electrode pair in IMS-ADD (in addition to the longitudinal voltage component), according to two embodiments of the invention: an ideal rectangular profile (a), a bisinusoidal profile created by superposition of two harmonics (b).
Figure 2B:
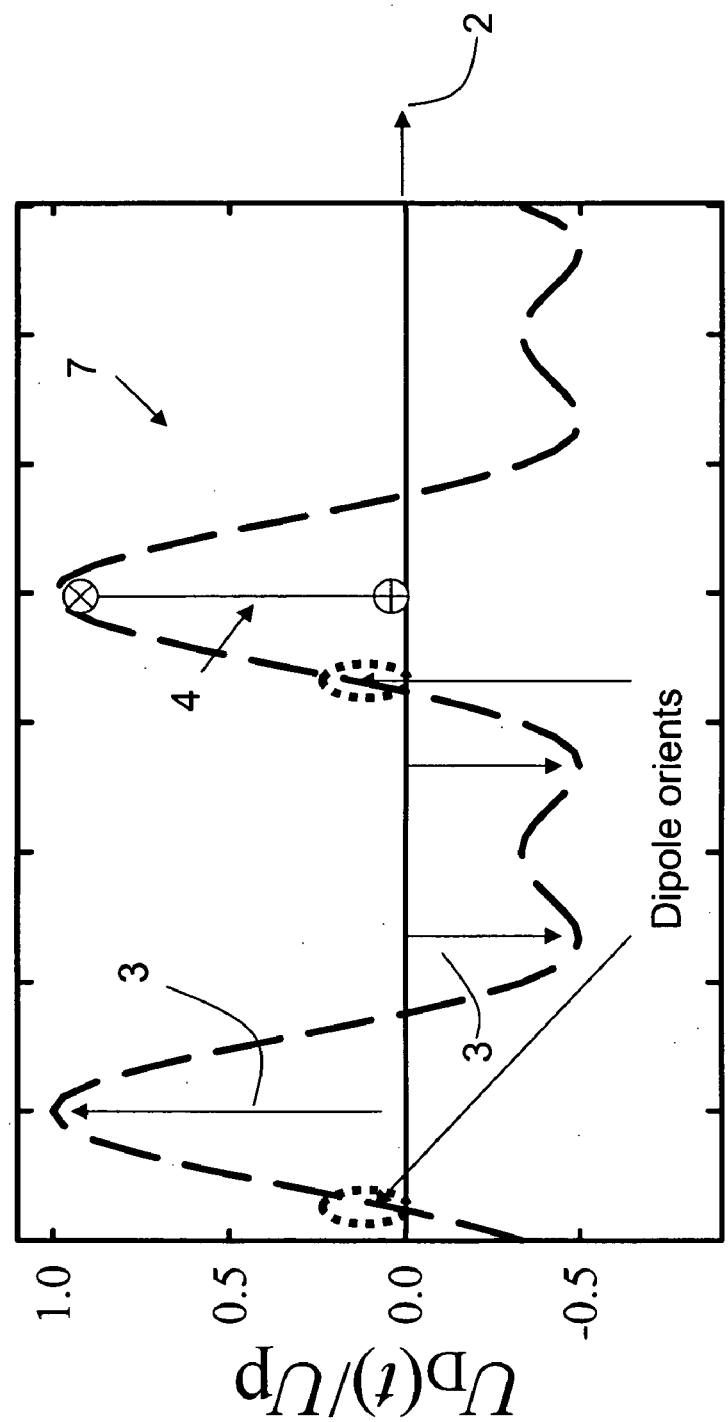

FIG. 2a illustrates an ideal rectangular asymmetric waveform 6, applied to an IMS-ADD device as described hereafter in addition to the longitudinal drift field component 2, according to an embodiment of the invention. The strong aligning field component 3 orients the dipoles of analyte ions 4 thereby defining the alignment axis 3 at an angle to the drift axis 2. FIG. 2b illustrates a realistic asymmetric waveform 7 comprising a superposition of harmonic oscillations, applied to an IMS-ADD device as described hereafter in addition to the longitudinal drift field component 2, according to another embodiment of the invention. The waveform in FIG. 2b is of bisinusoidal type (i.e. an addition of two harmonic oscillations) with 2:1 frequency ratio and π/2 phase shift, but harmonics with other ratios, phase shifts, and/or other number of harmonics may equally be used without limitation.

Peak amplitudes $U_p$ of either symmetric or asymmetric waveforms 1, 5, 6, and 7 in FIGS. 1 and 2 must, at least, suffice to substantially align analyte ions, the highest possible amplitude maximizing the desired alignment. However, amplitudes are selected below the threshold causing electrical breakdown of IMS-ADD buffer gas, which depends on the pressure, temperature, nature, and purity of selected gas. The frequency and, to a lesser extent, amplitude are selected to ensure that, during each cycle, analyte ions remain well inside the analytical gap, or, in another mode described above, ions with direction-specific cross-sections along the alignment axis being below a desired value are filtered out of the device by neutralization at both electrodes. That value can be scanned during the experiment, achieving an IMS-ADD separation in two dimensions simultaneously, e.g. based on $\Omega^\perp$ and $\Omega\|$.

In addition to the criteria for a symmetric waveform, the $U_p$ of an asymmetric waveform intended for concurrent FAIMS/IMS-ADD separations must suffice to induce a requisite difference in ion mobility between high and low half-cycles. Such asymmetric waveforms may be generated by electrical hardware known in the FAIMS art. The CV is added to the waveform; scanning it would permit concurrent FAIMS/IMS-ADD separations.

Both symmetric and asymmetric waveforms may render the aligning field spatially either uniform or non-uniform along the alignment axis. A uniform field is achieved using planar electrodes, e.g., parallel planar electrodes described below [FIG. 3], and a non-uniform field requires curved electrodes, e.g., cylindrical and specifically coaxial cylindrical electrodes described below [FIG. 4]. A non-uniform asymmetric field of proper polarity (depending on the form of K(E) for the specific ion) induces ion focusing to the analytical gap median. A concurrent FAIMS/IMS-ADD separation in a non-uniform aligning field created by curved electrodes would reduce ion losses in the device, such as those due to diffusion and/or Coulomb repulsion.

Figure 3:
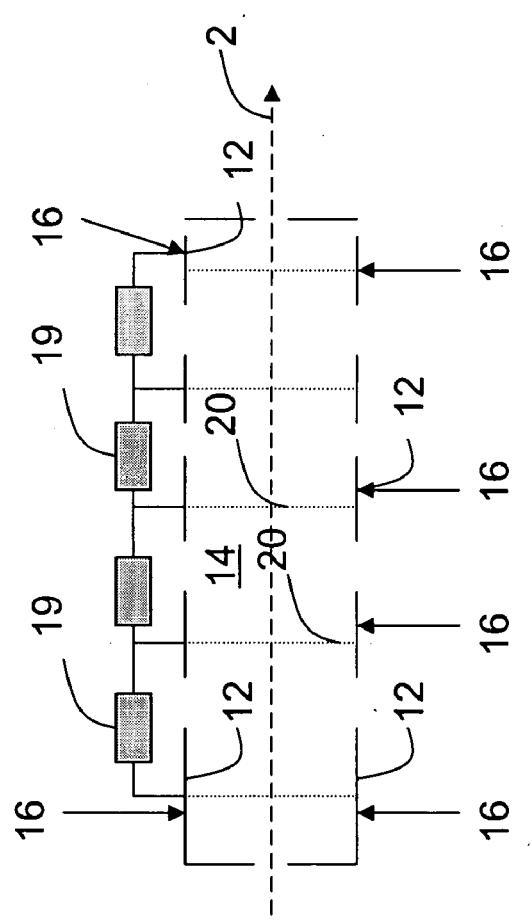
FIG. 3 presents a longitudinal cross-sectional view of an IMS-ADD device comprising two parallel planar segmented electrodes, according to an embodiment of the invention.

FIG. 3 presents a longitudinal, cross-sectional view of an IMS-ADD device 10, according to an embodiment of the invention. The device comprises planar segmented electrodes 12 with a space there-between (an analytical gap) 14 that ions traverse along the electrodes 12. Segments 16 carry individual voltages that create an electric field along the device, defining the drift field axis 18. Ions introduced into the analytical gap 14 traverse the device 10 passing between successive segments 16. A substantially uniform drift field 2 is generated when widths of segments 16 along the drift direction are significantly less than the width of the analytical gap 14. A DC (time-independent) drift field 2 may be achieved by consecutively linking all segments 16 using a series of resistors 19 of sufficiently high resistance (i.e. a voltage divider) and applying a drift voltage to the first and last segments 16 of device 10. To create a near-uniform field, identical resistors 19 are used. Selection of resistors 19 depends on the number of electrode segments 16, the IMS-ADD drift voltage, current output limitations of the power supply, the need for resistor heat dissipation, and other factors, as will be understood by those skilled in the art. While electrodes 12 illustrated in FIG. 3 are parallel, slightly non-parallel electrodes 12, defining an analytical gap 14 that narrows or widens along the device 10, may be beneficial in a concurrent FAIMS/IMS-ADD operation by improving the resolution and peak capacity in the FAIMS dimension. In another embodiment, the drift field 2 is non-uniform, e.g., to achieve collisional fragmentation and/or DC focusing of ions at IMS-ADD terminus. This may be established using non-identical resistors 19 or a separate power supply. All electrode and/or resistor combinations as will be selected by those skilled in the art are hereby incorporated.

Alternatively, voltages on some or all segments 16 may be set directly by computer-controlled power supplies, allowing IMS-ADD separations that employ time-dependent longitudinal fields such as a traveling wave or ledge. Separations using a time-dependent drift field can offer certain advantages over those employing a DC field, such as lower drift voltage and smaller device sizes. The invention is not restricted to any specific form of longitudinal drift field 2, which must only (a) be weak enough not to materially interfere with the dipole orientation by the aligning field component 20 and (b) strong enough to effect a sufficient separation of aligned ions by their direction-specific cross sections.

As described above, an IMS-ADD waveform comprises a strong aligning component 3 and a relatively weak drift component 2. For either a symmetric or an asymmetric waveform, the component 3, in the case of asymmetric waveform with the addition of appropriate CV, is applied to pairs of device electrodes (e.g., 12) without account for segmentation, i.e. equally to all segments (e.g., 16) of either electrode of a pair. The component 2 is partitioned across the segments (e.g., 16) of device electrodes (e.g., 12) as described above. The electronics that co-applies RF and DC potentials (including, but not limited to a uniform ladder of DC voltages) in various modes to a series of electrodes is well-known in the MS art, e.g., as implemented with the electrodynamic ion funnel (Smith et al., U.S. Pat. No. 6,107,628), incorporated herein by reference in its entirety.

Figure 4:
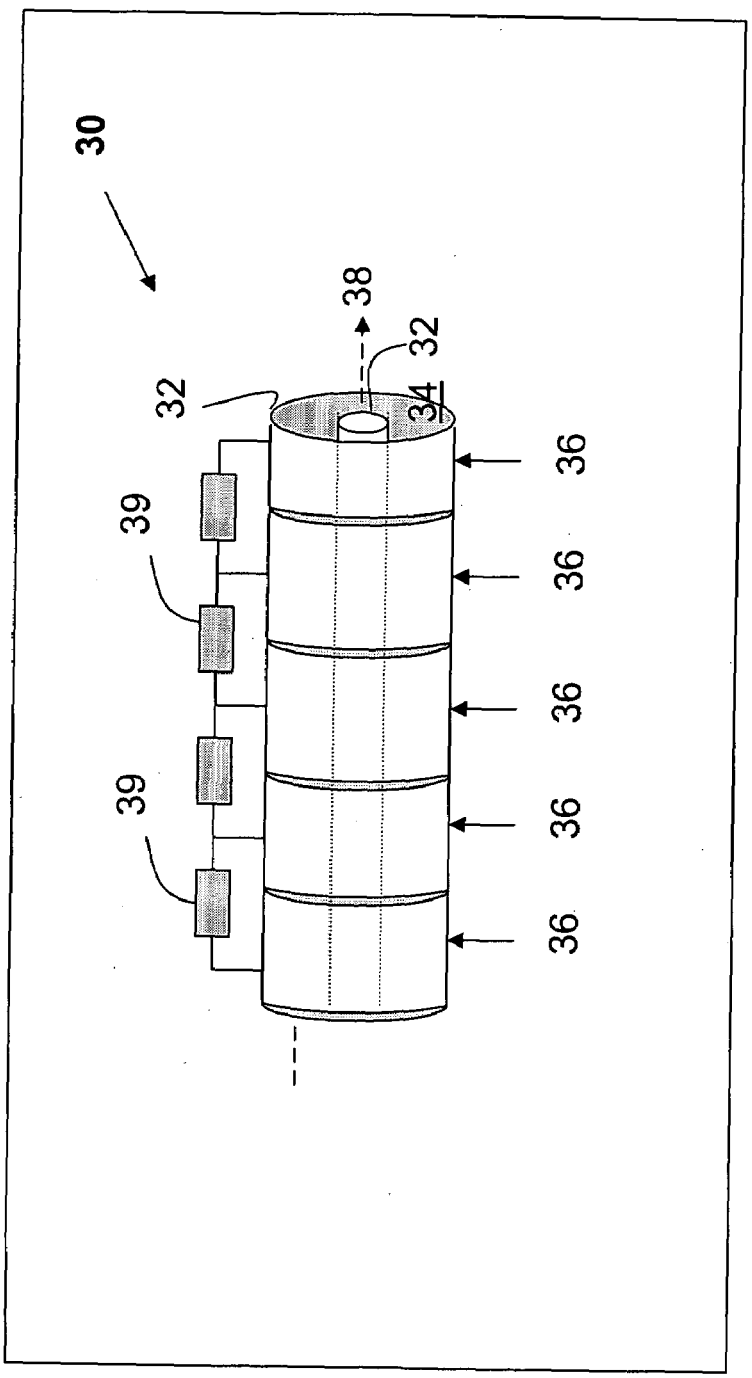
FIG. 4 presents a longitudinal cross-sectional view of an IMS-ADD device comprising two coaxial cylindrical segmented electrodes, according to another embodiment of the invention.

FIG. 4 presents a longitudinal, cross-sectional view of an IMS-ADD device 30, according to another embodiment of the invention. The device 30 comprises two coaxial axially segmented electrodes 32, for example of cylindrical geometry. Electrodes 32 contain an annular space there-between (analytical gap) 34 that ions traverse, passing by successive segments 36, parallel to the axis 38. Other engineering aspects, including, e.g., the selection of resistors 39, are as for the planar electrode device 10, described above with respect to FIG. 3. In concurrent FAIMS/IMS-ADD operation described above, this embodiment creates a non-uniform aligning field needed for ion focusing. While electrodes 32 as depicted in FIG. 4 are cylindrical, making one or both slightly conical, i.e., creating an analytical gap 34 that narrows or widens along the device, may benefit the concurrent FAIMS/IMS-ADD operation by improving the resolution and peak capacity in the FAIMS dimension. All electrode 32 configurations as will be selected by those skilled in the art are incorporated.

The electric field ($E_a$) needed to significantly align an electric dipole with moment p is evaluated using equation [6]:

$$E_a = k \times T/p \qquad [6]$$

The field must be strong enough to overcome the energy of random thermal rotation that, on average, equals $k \times T$ (around the two axes orthogonal to the dipole) and thereby align ("lock") the dipole. Thermal rotational energies of individual ions have a finite distribution about the $k \times T/2$ average per degree of freedom, and securely locking an overwhelming majority of a statistical ensemble requires $E > (2-3) \times E_a$. Thus, IMS-ADD waveforms should best have the peak amplitude defined by equation [7]:

$$U_p >> d \times k \times T/p, \qquad [7]$$

where d is the analytical gap width. However, a substantial alignment as defined herein would already be found at $E=E_a$ and $U_p=d \times k \times T/p$. The electrical breakdown of $N_2$ or air at STP occurs at 3–4 kV/mm (Meek et al., *Electrical Breakdown of Gases*, Wiley, NY, 1978), which, by equation [6], substantially aligns dipoles with p values over ~250 Debye (D). On average, p values are higher for larger species. For small molecules, p values tend to be under ~30 D (e.g., 15 D for amino acid glycine). For proteins, p values typically range within ~100–4000 D, with the mean value of entries in the Protein Data Bank (the most comprehensive database of proteins available from [http://www.rcsb.org/pdb]) being 628 D. For example, p for Cytochrome C, a common midsize protein of 12.4 kDa mass, is 528 D. Hence a 3–4 kV/mm field will align most proteins.

Dipoles smaller than ~300 D may be aligned in a buffer gas that resists electrical breakdown better than $N_2$ or air, and thus supports a stronger aligning field. For example, sulfur hexafluoride ($SF_6$) at STP allows fields as high as E~10 kV/mm, i.e. ~2.5 times stronger than in air (Meek et al., ibid) that align dipoles with p values over ~100 D, covering essentially all proteins. In situations where pure $SF_6$ may be impractical, mixtures involving $SF_6$ (such as $N_2/SF_6$ or air/$SF_6$) provide most of the benefit sought (Meek et al., ibid). Other gas-phase insulators (that may perform even better than $SF_6$) may also be used.

Smaller dipoles can be aligned by increasing the buffer gas pressure that raises the electrical breakdown threshold by increasing N in proportion to P by the ideal gas law (Meek et al., ibid). For example, $N_2$ at P=5 atm holds E~15 kV/mm, i.e. ~4–5 times higher than at STP, which aligns dipoles with p values over ~60 D, again covering essentially all proteins.

Still smaller dipoles can be aligned by cooling the buffer gas. Cooling is extremely effective as it both raises the electrical breakdown threshold (by increasing N in proportion to 1/T by the ideal gas law) and decreases the field needed for dipole alignment (in proportion to T, by equations [6, 7]). For example, $N_2$ at P=1 atm and T~80 K (close to the boiling point) holds E>10 kV/mm, which would align dipoles with p values over ~25 D. Hydrogen is a reasonable gas-phase insulator that can be cooled down below 80 K and specifically to ~25 K (at P=1 atm.). Under those conditions, the gas would support E>30 kV/mm, which aligns dipoles as small as p~3 D, covering virtually all bio- and macromolecular species including peptides, proteins, oligonucleotides, DNA, RNA, oligosaccharides, polymers, dendrimers, almost all metabolites, as well as many small inorganic and organic ions.

In a concurrent FAIMS/IMS-ADD operation mode, providing the gas medium with best properties for IMS-ADD analyses may have to be balanced with the optimization of separation in the FAIMS dimension. For example, some gases resistant to electrical breakdown and thus suitable for IMS-ADD might provide poor FAIMS separations for particular analytes because of near-flat K(E) curves. However, in general both IMS-ADD and FAIMS separations benefit from the highest electric field and $U_p$ possible. In particular, gas-phase electric insulators containing $SF_6$ and/or other electron scavengers can prove useful. Separations in the FAIMS dimension may be further enhanced in certain gas mixtures in which high-field ion mobilities exhibit a significant non-Blanc behavior, or by admixing vapors of water or volatile organics in the gas.

As described above, IMS-ADD separations may be extended to medium-size and even small ions by judicious choice of gas composition, pressure, and temperature that permit increasing the dipole alignment. The minimum p values quoted above are for permanent dipole moments and exclude the induced dipole that always augments the permanent dipole. So these calculations undervalue the total dipole and thus likely overestimate the electric field, the value of $U_p$ needed for alignment, and the minimum p that could be aligned. The utility of IMS-ADD may thus prove broader than these conservative calculations indicate, and no limitation as to the lowest dipole moment or smallest ion to which this disclosure applies is intended.

When the field of aligning waveform (whether symmetric or not) changes direction, inversion of the ion orientation takes a finite time because of both rotational inertia of the ion and a finite gas viscosity. That relaxation time, $t_{rel}$, is calculable from molecular geometry and shear viscosity, $\eta_0$, using the Stokes-Einstein relation (Halle et al., *Proc. Nat'l Acad. Sci USA* 100, 12135, 2003). For an estimate, one may assume a spherical geometry, wherein, by equation [8]

$$t_{rel} = k \times T/(6\eta_0 V) \qquad [8]$$

where V is the molecular volume. For proteins of less than ~200 KDa weight in air or $N_2$ at STP ($\eta_0=17.4\times10^{-6}$ Pa×s), $t_{rel}$ would be under ~5 ns, i.e. a factor of ~$10^2$–$10^3$ less than typical waveform periods. Hence, finite relaxation times should be nearly immaterial in IMS-ADD. This renders the measured direction-specific cross-sections nearly insensitive to waveform frequency and greatly simplifies their modeling, e.g., for assignment of ion geometries. Relaxation times might be more significant for extremely large (MDa range) macromolecular ions and viscous gases, for example heavy gases (such as $SF_6$) and gases at high pressures and/or low temperatures. Relaxation effects can be accounted for in the direction-specific cross section calculations by appropriate orientational averaging of collision integrals during the relaxation time that differs from the averaging in a steady-state aligned regime.

From simulations, a practical IMS-ADD or concurrent FAIMS/IMS-ADD device may have d~0.25–4 mm and more particularly ~0.5–2.5 mm. Then the necessary aligning field may be provided by $U_p$~100 V–50 kV and more particularly ~500 V–6 kV, depending on d and gas properties (identity, pressure, and temperature). The frequency of waveform (whether symmetric or asymmetric) may be ~50 kHz–3 MHz, and more particularly ~100 kHz–1.5 MHz, depending on d, $U_p$, and gas properties. The widths of electrode segments along the drift direction could be ~0.1–4 mm and more particularly ~0.3–1.5 mm. All those parameters could be optimized, depending on specific priorities and engineering constraints, within a flexible computational environment for simulation of FAIMS analyzers (Shvartsburg et al., *J. Am. Soc. Mass Spectrom.* 15, 1487, 2004).

The resolving power of IMS-ADD is set by equation [9]:

$$R = t_D/[t_i^2 + t_r^2 + (t_D/R_d)^2]^{1/2} \qquad [9]$$

where $t_D$ is the drift time through the device, $t_i$ is the (temporal) width of initial ion packet, $t_r$ is the detector response time (for example, the pusher period for a time-of-flight MS detector), and $R_d$ is the diffusion-limited resolving power ideally given by equation [10]:

$$R_d = [LE_d ze/(16kT ln 2)]^{1/2} \qquad [10]$$

where L is the analytical gap length, $E_d$ is the drift field intensity, and ze is the ionic charge. The strategies for maximizing IMS-ADD resolution include reducing $t_i$ and $t_r$, raising $E_d$ (up to a certain point) and L, and cooling the gas. If IMS-ADD is intended as a structural probe, $E_d$ would be restricted by the need to remain in the low-field limit where K(E) is constant and equation [5] applies. Also, the resolution would deteriorate at high $E_d$, falling below the predictions of equations [9] and [10] because of stronger longitudinal ion diffusion at high E/N. The $E_d$ value is also set below the threshold for electrical breakdown in gas, which should be automatic as drift field must be significantly weaker than the aligning field. The IMS-ADD length is constrained by engineering limitations and ion losses due to diffusion and Coulomb repulsion that increase with increasing L unless effective ion focusing is implemented, e.g. using ion funnels. As is known in the art, cooling of buffer gas is limited by hardware considerations, availability of appropriate heat transfer fluids, and the onset of massive gas condensation on analyte ions. However, cooling to ~80 K using liquid $N_2$ is well-known. Notably, reducing T that greatly facilitates the dipole alignment as discussed above also serves to maximize the IMS-ADD resolution.

In practice, L may be selected in the range of ~1–200 cm, and more particularly ~2–30 cm, depending on the gas properties. The DC drift voltage is selected in the range of ~10 V–10 kV (depending on L and gas properties), creating an $E_d$ value in the range of ~1–1000 V/cm. The $t_i$ value may then be in the range of ~1 μs–1 ms and particularly ~5–100 μs, depending on $t_D$. In the time-domain mode, ion packets are injected into IMS-ADD with a period beyond the longest $t_D$ of any analyte species. In targeted separations (for example, when studying the conformations of a particular ion), often all to fall within a relatively narrow range. Then several ion packets could be "stacked" in IMS-ADD by more frequent injections and separated simultaneously. Alternatively to the time-domain mode, a frequency-domain mode may be used wherein the analyte $t_D$ spectrum is a Fourier transform of raw data obtained by scanning the frequency of ion injections. The frequency-domain mode can hold a significant sensitivity advantage over the time-domain mode because of a higher duty cycle, possibly reaching 50%. This mode and its variations, e.g., employing Hadamard or other transforms instead of Fourier transform, equally apply to IMS-ADD, and all such modifications are incorporated without limitation. The ranges of IMS-ADD parameters given here and above are merely examples anticipated to provide good results within reasonable engineering, compatibility, and cost constraints; other values for any and all said parameters may be chosen within the scope of the invention.

The direction-specific cross sections measured for any angle between the alignment and drift axes in IMS-ADD can be matched with values calculated for candidate geometries. Those values may be computed using the expression for scattering angle of buffer gas atoms on the ion ($\chi$) as a function of ion-atom relative velocity g, impact parameter b, and the angles $\theta$ and $\gamma$ defining the collision geometry. To obtain the direction-specific cross sections relevant to IMS-ADD (e.g., $\Omega^\perp$ and $\Omega\|$) the convolutions over $\theta$ and/or $\gamma$ in the integration of function $\chi(g, b, \theta, \gamma)$ over the four variables are set up to properly reflect a non-random representation of all collision geometries due to dipole alignment (remembering that ions still freely rotate around the dipole axis). This is achievable within a Monte Carlo integration scheme. Sources of plausible trial geometries may be NMR and X-ray, solution spectroscopies (e.g., circular dichroism, electric birefringence, fluorescence depolarisation, dynamic light scattering, and others), MS/MS including electron capture dissociation (ECD), other gas-phase data [e.g., hydrogen/deuterium (H/D) exchange, photoelectron spectroscopy (PES), conventional IMS, and FAIMS], and molecular modeling. All such sources as would be selected by a person skilled in the art are hereby incorporated without limitation.

Figure 5A:
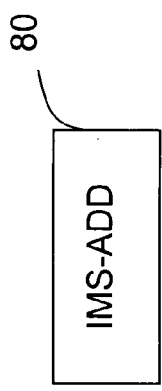
FIGS. 5a–5c illustrate three exemplary system configurations according to embodiments of the invention: a standalone IMS-ADD device (a), an IMS-ADD device coupled to an ESI source (b), an ESI/IMS-ADD device coupled to a mass-spectrometer (c).
Figure 5B:
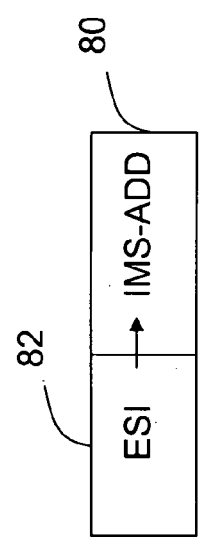

In operation, IMS-ADD devices can be flexibly coupled to various other analyzers and stages known in the art of mass spectrometry and analytical chemistry. FIG. 5a illustrates a stand-alone IMS-ADD device 80. FIG. 5b illustrates the IMS-ADD device 80 coupled with an ion source 82 selected from the group including, but not limited to, electrospray ionization (ESI), thermo- or sonic spray, matrix-assisted laser desorption ionization (MALDI or AP-MALDI), surface-enhanced laser desorption ionization (SELDI), laser vaporization or desorption, surface or secondary ion ionization, photoionization and atmospheric pressure photoionization (APPI), arc discharge, coronary or cathode discharge, electron impact (EI), chemical ionization (CI or APCI), liquid evaporation/clustering, "pick-up", or any other ion production or ionization mechanism. The manner by which analyte ions are generated is immaterial to the present invention and by no means should it be limited to operation with any particular ion source. In the instant embodiment, (non mass-selected) ions arriving to the IMS-ADD terminus are registered using known means standard to the conventional IMS art, such as Faraday cup collectors (Hill et al., Anal. Chem. 62, 1201A, 1990).

Analyte ions are injected into an IMS-ADD device in discrete packets. Ion beams may be already pulsed, such as those arriving from a pulsed source (for example, MALDI) or another separations stage providing discrete ion packets (for example, conventional IMS). Continuous (and certain pulsed) ion beams are converted into discrete packets prior to injection into IMS-ADD. This conversion can be accomplished using many means known in the art, including, but not limited to, mechanical shutters, electrostatic shutters such as pulsed ion retarding/repelling wires, mesh or electrode(s), a Bradbury-Nielsen gate, a split lens for transverse ion deflection, and a t-FAIMS. At moderately high pressure, ions may be accumulated and periodically injected into IMS-ADD by means of an ion funnel, and in particular an hourglass funnel useful for pulsed ion transmission. Ions may also be conveyed into IMS-ADD using other methods and devices known in the art for MS, IMS and FAIMS, including, but not limited to, orifice-skimmer cones (OSC) and curtain gas interfaces. The specific means and methods employed to introduce discrete ion packets into IMS-ADD and/or accumulate ions for such introduction are immaterial to the present invention, and no limitation to operation with any particular method or implement is intended.

Pressure in an IMS-ADD device is selected to best slightly exceed that in the preceding chamber, so that there is a continuous gas flow out of IMS-ADD device opposing the motion of entering ions. This flow prevents the contamination of IMS-ADD buffer gas by outside gases, and prohibits neutrals from entering the device where they can become ionized via charge-transfer from analyte ions, resulting in erroneous measurements. Thus the buffer gas leaks out of IMS-ADD through an entrance and (if present) exit orifice, and is continuously replenished. A counterflow of buffer gas inside IMS-ADD may somewhat improve the resolution through the increase of separation time. The pressure in IMS-ADD and gas flow into it may be controlled by standard gas pressure and flow valves, and monitored by means known in the art, such as capacitance manometers, e.g. those commercially available from MKS Instruments (Wilmington, Mass.).

Figure 5C:
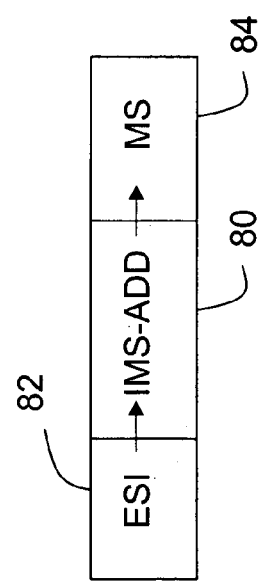
Figure 6C:
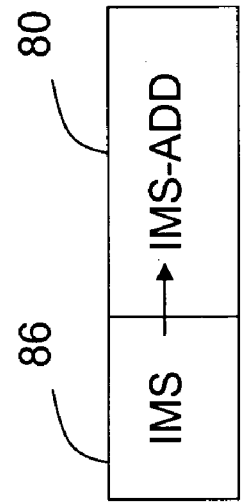
FIGS. 6a–6d illustrate various embodiments of the invention involving online 2-D gas-phase separations: an IMS-ADD device preceding an IMS analyzer (a), IMS-ADD following an IMS analyzer (b), IMS-ADD preceding a FAIMS analyzer (c), and IMS-ADD following a FAIMS analyzer (d).
Figure 6D:
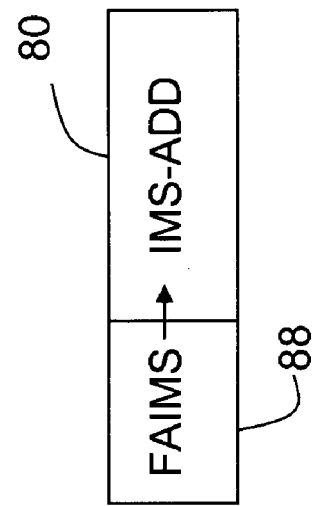
Figure 6A:
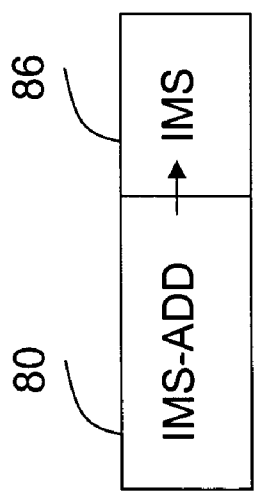
Figure 6B:
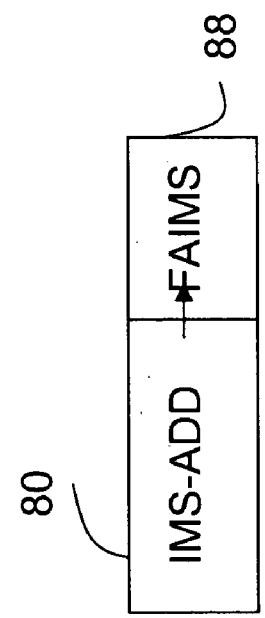
Figure 7A:
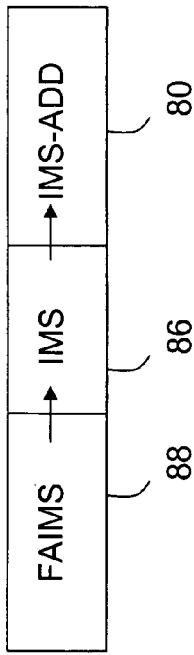
FIGS. 7a–7f illustrate various embodiments of the invention involving online 3-D gas-phase separations: an IMS-ADD device preceding an IMS/FAIMS tandem (a), IMS-ADD preceding a FAIMS/IMS tandem (b), IMS-ADD following an IMS/FAIMS tandem (c), IMS-ADD following a FAIMS/IMS tandem (d), IMS-ADD between IMS and FAIMS (e), and IMS-ADD between FAIMS and IMS (f).
Figure 7B:
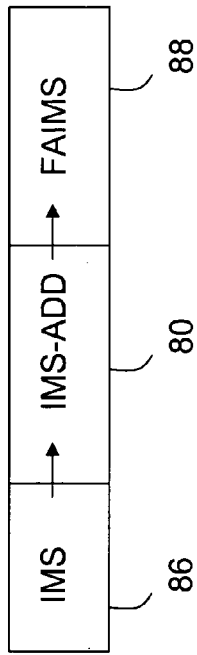
Figure 7D:
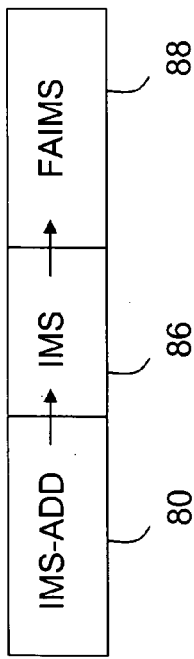
Figure 7E:
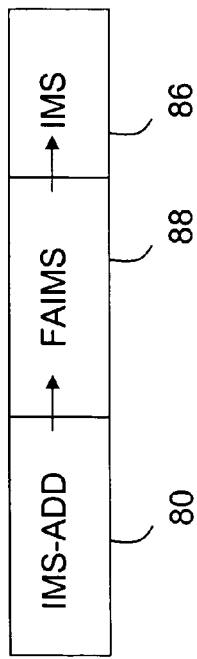
Figure 7C:
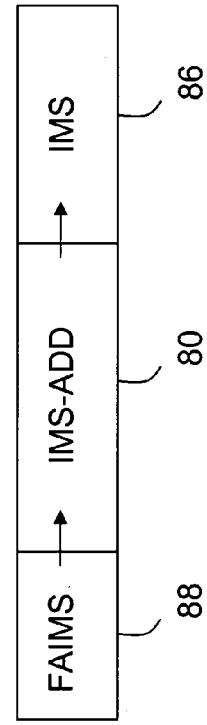
Figure 7F:
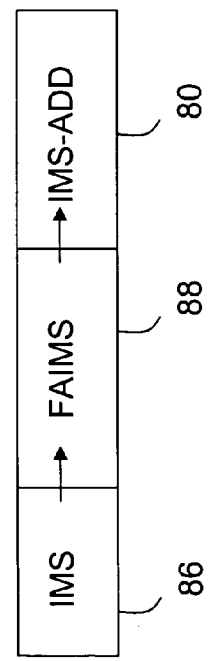

In another embodiment illustrated in FIG. 5c, IMS-ADD device 80 is interfaced to an MS analyzer 84. The analyzer 84 may operationally follow IMS-ADD device 80 (as illustrated) whereby ions separated in IMS-ADD are submitted for MS analyses. Alternatively, MS analyzer 84 may precede IMS-ADD device 80 whereby mass-selected ions are supplied to IMS-ADD. The MS analyzer 84 may be of any type, including but not limited to sector, quadrupole, time-of-flight (ToF), quadrupole trap, orbitrap, Fourier-transform ion cyclotron resonance (FTICR), or any combination thereof. In the case of a ToF MS analyzer, the dynamic range and/or IMS resolution would be improved by employment of position-sensitive and multi-anode ToF detectors. Coupling to MS can be made in conjunction with other instruments, devices, tools, software, reagents, and/or consumables as will be selected by a person skilled in the art, without limitation. In particular, a second ion gate may be installed at or near the IMS-ADD 80 exit to more accurately measure the ion drift time through the device 80. The specificity of IMS-ADD/MS analyses may be enhanced by ion spectroscopies, such as photoelectron spectroscopy (PES) and photo-dissociation spectroscopy.

In yet other embodiments illustrated in FIGS. 6a–6d, IMS-ADD is coupled to IMS and/or FAIMS in various configurations effecting multi-dimensional, e.g., two-dimensional (2-D) or three-dimensional (3-D), gas-phase ion separations that augment the peak capacity and specificity of analyses. In arrangements involving IMS-ADD and either IMS or FAIMS, an IMS-ADD device 80 may either precede IMS device 86 (FIG. 6a) or FAIMS device 88 (FIG. 6b), or follow IMS device 86 (FIG. 6c) or FAIMS device 88 (FIG. 6d), allowing for four possible tandem configurations that provide 2-D ion separations. In one embodiment, a planar FAIMS device 88 is used. In another embodiment, a cylindrical FAIMS device 88 is used. FAIMS devices of other geometries may equally be coupled, without limitation.

In configurations involving IMS-ADD and both IMS and FAIMS illustrated in FIGS. 7a–7f, an IMS-ADD device 80 may precede the IMS 86/FAIMS 88 or FAIMS 88/IMS 86 hybrids (FIG. 7a and FIG. 7b, respectively), follow them (FIG. 7c and FIG. 7d, respectively), or be inserted between IMS 86 and FAIMS 88 with either preceding IMS-ADD 80 (FIG. 7e and FIG. 7f), allowing six possible configurations that provide 3-D ion separations. These configurations permit separations of analyte ions by direction-specific cross sections in IMS-ADD 80, ion mobility in IMS 86, and CV in FAIMS 88, or any pair of that set. Any of the configurations disclosed herein may further be coupled, e.g., to a gas chromatograph (GC), preceding it, following it, or inserted between any of the individual devices. In addition, any of the configurations may further be coupled to an MS analyzer and/or other spectrometer of any type preceding it, following it, or inserted between any of the constituent devices, achieving separation in two or three dimensions coupled with MS analyses, gas chromatography, and/or spectrometry.

Figure 8B:
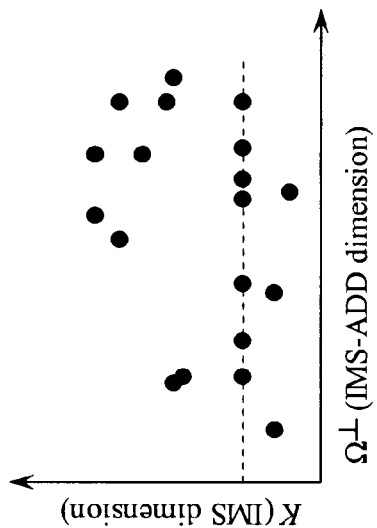
FIGS. 8a–d schematically presents a 3-D gas-phase separation in IMS, FAIMS, and IMS-ADD dimensions (d)
Figure 8D:
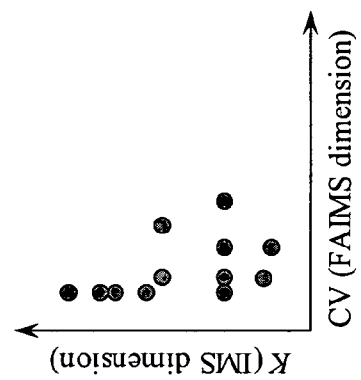
Figure 8A:
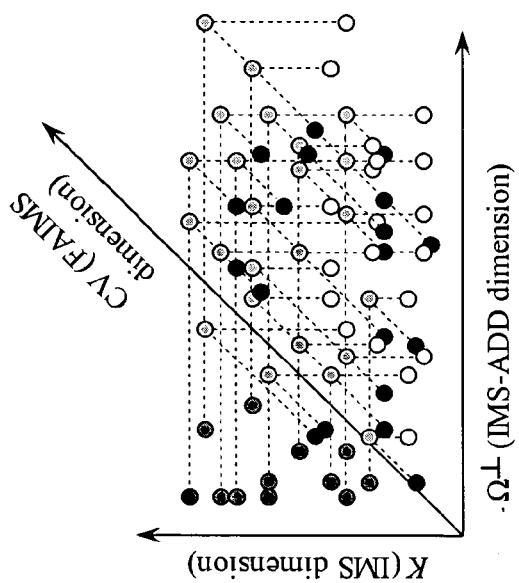
Figure 8C:
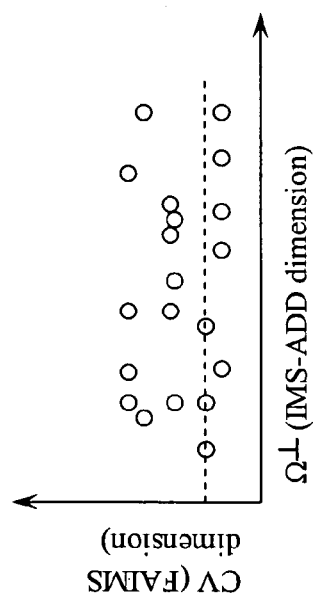

The utility of 2-D and 3-D gas-phase separations involving IMS-ADD is illustrated in FIGS. 8a–8d. FIG. 8a presents an exemplary plot of a hypothetical ion mixture separated in 3 dimensions: IMS-ADD of the present invention, conventional IMS, and FAIMS. The sample contains 24 components that are all separated in 3-D analyses (grey circles). FIGS. 8b–8d present plots of all three partial 2-D separations of the same mixture, in dimensions of: IMS-ADD of the present invention and conventional IMS (FIG. 8b), IMS-ADD and FAIMS (FIG. 8c), and conventional IMS and FAIMS (FIG. 8d). The number of fully separated species is 18 (FIG. 8b), 18 (FIG. 8c), and 10 (FIG. 8d). Hence, none of the three 2-D methods distinguishes all 24 species present in the sample, identified by 3-D separations involving IMS-ADD. Of course, IMS-ADD is still useful in 2-D separations. For example, 7 different ions that have identical values of K and thus are indistinguishable in conventional IMS are separated in IMS-ADD/IMS (FIG. 8b), and 3 different ions that have identical CV values and thus are indistinguishable in FAIMS are separated in IMS-ADD/FAIMS (FIG. 8c).

In yet another embodiment (not shown), a concurrent FAIMS/IMS-ADD device described above is coupled to (either preceding or following) conventional IMS 86 to effect 3-D gas-phase separations using two stages only, which reduces the number of interfaces thus reducing ion losses and improving sensitivity. This hybrid device may be optionally coupled to MS analyzers and/or spectrometers of any type that preceed it, or follow it, or are inserted between the two stages.

Two or more IMS-ADD devices 80 configured with different angles between the alignment and drift axes (in particular, but not necessarily $\beta=0°$ and $\beta=90°$) may be coupled to increase the peak capacity and specificity of analyses. Multiple IMS-ADD devices may be optionally interfaced with any or all of the conventional IMS 86, FAIMS 88, GC, and/or MS analyzers 84 in different sequential arrangements as disclosed above without limitation.

In any of the embodiments described herein, analyte ions may be dissociated inside, at the end of, or immediately past, the IMS-ADD device, with fragments registered or passed on to MS and/or other separation or analysis stages. This may increase the orthogonality of IMS-ADD to other methods, and/or provide complementary information about ions. Ion dissociation may be effected using, e.g., collisional, thermal, field, photo, or electron capture dissociation, or other known mechanisms without limitation. In particular, dissociation may be induced by means known in the art including, but not limited to, collision cells, orifice-skimmer cones, or high-field (split-field) regions. The specific dissociation mechanism and hardware effecting it are immaterial to the present invention, which is by no means limited to operation with any particular method for ion dissociation.

An IMS-ADD device, by itself or coupled with any or all other gas-phase separation methods and MS analyzers or spectrometers as disclosed herein, may be preceded either online or offline by one or more stages of condensed-phase separations upfront of an ion source, including, but not limited to, normal and reversed phase liquid chromatography (LC), strong-cation exchange (SCX), supercritical fluid chromatography (SFC), capillary electrophoresis (CE), capillary isoelectric focusing (CIEF), gel electrophoresis in one or two dimensions such as SDS polyacrylamide gel electrophoresis (SDS-PAGE), 2-D gel, and combinations thereof. All analytical devices and techniques as will be selected by a person skilled in the art are hereby incorporated. Such configurations further increase the peak capacity and specificity of analyses, and improve the sensitivity and dynamic range by reducing charge competition due to unequal ionization efficiency of different analytes (ionization suppression)—a ubiquitous problem well-known in the art related to ion sources such as ESI and MALDI. It will be apparent to those skilled in the art that IMS-ADD comprehends both the mechanical embodiments and the application of waveforms described herein. Thus, no limitation is intended to disclosures of specific embodiments herein.

We claim:

1. A method for separation and analysis of gas-phase ions, comprising:
   providing a plurality of electrodes containing a space therebetween, said electrodes carrying voltages establishing an electric field over at least a part of said space, said field comprising a first component along a first (drift) axis superposed over a second substantially stronger component along a second (alignment) axis, said second axis disposed at a defined angle relative to said first axis;

filling at least a portion of said space with a buffer gas;

periodically introducing into said space a discrete packet of analyte ions comprising at least one species therein having an electric dipole, wherein said second field component substantially aligns said dipole(s) of said at least one species along said second axis, and said first component pulls said substantially aligned ions along the direction of said first axis; and whereby said ions are spatially separated or identified based on a measured collision cross section with gas molecules that is other than averaged equally over all spatial orientations and is direction-specific depending on said defined angle.

2. The method of claim 1, wherein said first component is a time-independent DC field.

3. The method of claim 1, wherein said first component is a time-dependent field, including a traveling ledge or wave, that effects ion separation in either a time or a frequency domain.

4. The method of claim 1, wherein said first component has intensity in the range from about 1 V/cm to about 5000 V/cm.

5. The method of claim 4, wherein said first component has intensity in the range from about 10 V/cm to about 1000 V/cm.

6. The method of claim 1, wherein said component is a time-dependent oscillatory function.

7. The method of claim 6, wherein said function is a harmonic waveform.

8. The method of claim 6, wherein said function is a rectangular waveform or an approximation thereof comprising a superposition of two or more harmonic waveforms having different frequencies.

9. The method of claim 6, wherein said function is symmetric with respect to zero field.

10. The method of claim 6, wherein the frequency, amplitude, and/or waveform profile of said oscillatory function are set to filter out ions having direction-specific cross sections along said second component that are below a particular desired value.

11. The method of claim 10, wherein said frequency, amplitude, and/or waveform profile of said function are varied producing a two-dimensional IMS-ADD separation based on direction-specific cross sections along said first and second components simultaneously.

12. The method of claim 6, wherein said function is asymmetric with respect to zero field.

13. The method of claim 12, wherein said function features an adjustable voltage superposed on top of a fast oscillation, a slow variation of said voltage yielding a spectrum in the 1$^{st}$ dimension of concurrent FAIMS/IMS-ADD separation.

14. The method of claim 12, wherein said gas is a gas mixture and/or contains volatile vapors wherein high-field mobilities of said analyte ions exhibit a significant non-Blanc behavior improving the separation in the 1$^{st}$ dimension of concurrent FAIMS/IMS-ADD analyses.

15. The method of claim 6, wherein said second component is spatially non-uniform along its direction and said function is asymmetric with respect to zero field and has a polarity to induce ion focusing to the median of said space during separation.

16. The method of claim 6, wherein the oscillation frequency of said oscillatory function is in the range from about 50 kHz to about 3 Mhz.

17. The method of claim 16, wherein the oscillating frequency of said oscillatory function is in the range from about 100 kHz to about 1.5 MHz.

18. The method of claim 1, wherein the peak intensity of said second component exceeds the quantity k×T/p to achieve optimum dipole locking.

19. The method of claim 18, wherein the peak intensity of said second component exceeds the quantity 2k×T/p to achieve optimum dipole locking.

20. The method of claim 1, wherein the peak intensity of said second component is in the range from about 0.3 kV/mm to about 30 kV/mm.

21. The method of claim 20, wherein the peak intensity of said second component is in the range of about 1 kV/mm to about 10 kV/mm.

22. The method of claim 1, wherein said defined angle is either 0 degrees or 90 degrees.

23. The method of claim 1, wherein said gas is an electrical insulator selected from the group consisting of $SF_6$, other electron scavengers, and/or mixtures thereof with other gases, including air, nitrogen, oxygen, helium, hydrogen, or mixtures thereof.

24. The method of claim 1, wherein said gas is pressurized to above-atmospheric pressure to raise the electrical breakdown threshold.

25. The method of claim 1, wherein said gas is cooled below ambient temperature to a temperature in the range from about 25 to about 300 K in order to facilitate the dipole alignment by reducing the thermal rotational energy and/or to raise the electrical breakdown threshold and/or to improve the IMS-ADD resolution.

26. The method of claim 25, wherein said gas is hydrogen or a mixture thereof with at least one other gas.

27. The method of claim 1, wherein said gas flows through said space in a direction opposite to said first component improving the resolution of an IMS-ADD separation.

28. The method of claim 1, wherein said discrete packets have a temporal width in the range from about 1 µs to about 1 ms.

29. The method of claim 28, wherein said discrete packets have a temporal width in the range from about 5 µs to about 100 µs.

30. The method of claim 1, wherein said discrete packets are introduced with a period shorter than the drift time of at least one of said ions through said space that multiple separating packets are stacked therein.

31. The method of claim 1, wherein, said analysis is performed in the frequency domain such that spectra of said analyte ions are transforms of raw data into the time-domain.

32. The method of claim 31, wherein said transforms are selected from the group consisting of Fourier transform and Hadamard transform.

33. The method of claim 1, wherein said discrete packets are formed using a member selected from the group consisting of mechanical shutter, electrostatic shutter, pulsed retarding/repelling wires, mesh, or electrode(s), Bradbury-Nielsen gate, split lens for transverse ion deflection, spherical FAIMS trap, electrodynamic ion funnel, hourglass funnel, or combinations thereof.

34. The method of claim 1, wherein said analyte ions introduced into said space are received directly or through other stages from a source selected from the group consisting of electrospray ionization, thermospray, sonic spray, matrix-assisted laser desorption ionization, atmospheric pressure matrix-assisted laser desorption ionization, surface-enhanced laser desorption ionization, laser vaporization, laser desorption, secondary ion ionization, photoionization, atmospheric pressure photoionization, arc discharge, coronary or cathode discharge, electron impact, chemical ionization, atmospheric pressure chemical ionization, liquid evaporation, liquid clustering, "pick-up", or combinations thereof.

35. The method of claim 1, wherein the pressure in said space exceeds that in an immediately preceding volume from which said analyte ions are introduced into said space, such that said gas flows out of said space in the direct opposite to the motion of said ions.

36. The method of claim 1, wherein at least some of said analyte ions are dissociated during, at the end of, or after analysis, by a member selected from the group consisting of collisional dissociation, thermal dissociation, field dissociation, photodissociation, electron capture dissociation, or combinations thereof.

37. The method of claim 1 sequentially coupled to one or more iterations of said method having different values for said defined angle in the range from 0 degrees to 90 degrees.

38. The method of claim 1, further sequentially coupled to at least one additional gas-phase method for ion separations and analysis selected from the group consisting of ion mobility spectrometry (IMS), field asymmetric waveform ion mobility spectrometry in devices of any geometry, mass spectrometry (MS) including tandem MS and multiple MS stages of any kind, gas chromatography (GC), photoelectron spectroscopy, photodissociation spectroscopy, and combinations thereof.

39. The method of claim 1 further coupled on-line or off-line to at least one additional method for separations and analysis of substances in solid or liquid phases selected from the group consisting of liquid chromatography (LC), normal phase LC, reversed phase LC, strong-cation exchange LC, supercritical fluid chromatography, capillary electrophoresis, capillary isoelectric focusing, gel separations in one or more dimensions, SDS-PAGE, 2-D gel, and combinations thereof.

40. The method of claim 1, wherein said analyte ions are biological or macro-molecular ions selected from the group consisting of proteins, protein complexes, peptides, polypeptides, oligonucleotides, DNA, RNA, polymers, oligosaccharides, dendrimers, and combinations and/or fragments thereof.

41. The method of claim 1 wherein said measured direction-specific cross sections are related to ionic structures by mobility calculations for candidate geometries derived from sources selected from the group consisting of NMR, X-ray, solution spectroscopies including circular dichroism, electric birefringence, fluorescence depolarization, dynamic light scattering, and the like, MS/MS including electron capture dissociation, or other gas-phase data including hydrogen/deuterium exchange, photoelectron spectroscopy, IMS, and FAIMS; theoretical modeling, and combinations thereof.

42. An apparatus useful for separation and analysis of gas-phase ions, comprising:
a plurality of electrodes containing a space between, said electrodes carrying voltages establishing an electric field over at least a part of said space, said field comprising a first component along a first (drift) axis superposed over a second substantially stronger component along a second (alignment) axis, said second axis disposed at a defined angle relative to the first axis, said space being operable for receiving a buffer gas filling at least a portion of said space, wherein when a discrete packet of analyte ions comprising at least one species therein having an electric dipole is periodically introduced into said space, said second field component substantially aligns said dipole(s) of said at least one species along said second axis, and said first component pulls said substantially aligned ions along the direction of said first axis; and whereby said ions are spatially separated or identified based on a measured collision cross section with gas molecules that is other than averaged equally over all spatial orientations and is direction-specific depending on said defined angle.

43. The apparatus of claim 42 wherein said first component is a time-independent DC field.

44. The apparatus of claim 42 wherein said first component is a time-dependent field including a traveling ledge or wave that effects ion separation in either a time or a frequency domain.

45. The apparatus of claim 42 wherein said first component has intensity in the range from about 1 V/cm to about 5000 V/cm.

46. The apparatus of claim 45 wherein said first component has intensity in the range from about 10 V/cm to about 1000 V/cm.

47. The apparatus of claim 42 wherein said second component is a time-dependent oscillatory function.

48. The apparatus of claim 47 wherein the oscillation frequency of said oscillatory function is in the range from about 50 kHz to about 3 MHz.

49. The apparatus of claim 48 wherein the oscillation frequency of said oscillatory function is in the range from about 100 kHz to about 1.5 MHz.

50. The apparatus of claim 42 wherein the peak intensity of said second component exceeds the quantity k×T/p to achieve optimum dipole locking.

51. The apparatus of claim 50 wherein the peak intensity of said second component exceeds the quantity 2k×T/p to achieve optimum dipole locking.

52. The apparatus of claim 42 wherein the peak intensity of said second component is in the range from about 0.3 kV/mm to about 30 kV/mm.

53. The apparatus of claim 52 wherein the peak intensity of said second component is in the range of about 1 KG/mm to about 10 KG/mm.

54. The apparatus of claim 42 wherein said defined angle is either 0 degrees or 90 degrees.

55. The apparatus of claim 42, wherein said gas is an electrical insulator selected from the group consisting of $SF_6$, other electron scavengers, and/or mixtures thereof with other gases including air, nitrogen, oxygen, helium, and hydrogen.

56. The apparatus of claim 42 wherein said gas is pressurized to above-atmospheric pressure to raise the electrical breakdown threshold.

57. The apparatus of claim 42, wherein said gas cooled below ambient temperature to a temperature in the range from about 25 to about 300 K in order to facilitate the dipole alignment by reducing the thermal rotational energy and/or raise the electrical breakdown threshold and/or improve the IMS-ADD resolution.

58. The apparatus of claim 42, wherein said discrete packets are formed using a member selected from the group consisting of mechanical shutter, electrostatic shutter, pulsed retarding/repelling wires, mesh, or electrode(s), Bradbury-Nielsen gate, split lens for transverse ion deflection, spherical FAIMS trap, electrodynamic ion funnel, hourglass funnel, or combinations thereof.

59. The apparatus of claim 42 wherein said analyte ions introduced into said space are received directly or through other stages from a source selected from the group consisting of electrospray ionization, thermospray, sonic spray, matrix-assisted laser desorption ionization, atmospheric pressure matrix-assisted laser desorption ionization, surface-enhanced laser desorption ionization, laser vaporization, laser desorption, secondary ion ionization, photoionization, atmospheric pressure photoionization, arc discharge, coronary or cathode discharge, electron impact, chemical ionization, atmospheric pressure chemical ionization, liquid evaporation, liquid clustering, "pick-up", or combinations thereof.

60. The apparatus of claim 42 sequentially coupled to one or more iterations of said apparatus having different values for said defined angle in the range from 0 degrees to 90 degrees.

61. The apparatus of claim 42, further sequentially coupled to at least one additional apparatus for gas-phase ion separations and analysis selected from the group consisting of implements for ion mobility spectrometry (IMS), field asymmetric waveform ion mobility spectrometry in devices of any geometry, mass spectrometry (MS), tandem MS, multiple MS stages of any kind, gas chromatography (GC), photoelectron spectroscopy, photodissociation spectroscopy, and combinations thereof.

62. The apparatus of claim 42 further coupled on-line or off-line to at least one additional apparatus for separations and analysis of substances in solid or liquid phases selected from the group consisting of implements for liquid chromatography (LC), normal phase LC, reversed phase LC, strong-cation exchange LC, supercritical fluid chromotography, capillary electrophoresis, capillary isoelectric focusing, gel separations in one or more dimensions, SDS-PAGE, 2-D gel, and combinations thereof.

* * * * *

UNITED STATES PATENT AND TRADEMARK OFFICE
CERTIFICATE OF CORRECTION

| | |
|---|---|
| PATENT NO. | : 7,170,053 B2 |
| APPLICATION NO. | : 11/097855 |
| DATED | : January 30, 2007 |
| INVENTOR(S) | : A A Shvartsburg, K Tang and R D Smith |

It is certified that error appears in the above-identified patent and that said Letters Patent is hereby corrected as shown below:

Column 1, lines 6 through 9 of the issued patent should read as follows:

The invention was made with Government support under grant number RR018522 from the U.S. National Institutes of Health and contract DE-AC05-76RL01830 awarded by the US Department of Energy. The government has certain rights in the invention.

Signed and Sealed this
Eleventh Day of September, 2012

David J. Kappos
*Director of the United States Patent and Trademark Office*